(12) United States Patent
Godek et al.

(10) Patent No.: US 9,126,891 B2
(45) Date of Patent: Sep. 8, 2015

(54) CYCLOALKYL-DIAMINES

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: MediSynergics, LLC, Newington, CT (US)

( * ) Notice: Subject to any disclaimer, the term of this patent is extended or adjusted under 35 U.S.C. 154(b) by 10 days.

(21) Appl. No.: 14/167,362

(22) Filed: Jan. 29, 2014

(65) Prior Publication Data

US 2015/0210626 A1 Jul. 30, 2015

(51) Int. Cl.
| | |
|---|---|
| *C07C 211/40* | (2006.01) |
| *C07D 307/52* | (2006.01) |
| *C07D 213/36* | (2006.01) |
| *C07D 231/12* | (2006.01) |
| *C07D 265/30* | (2006.01) |

(52) U.S. Cl.
CPC ............ *C07C 211/40* (2013.01); *C07D 213/36* (2013.01); *C07D 231/12* (2013.01); *C07D 265/30* (2013.01); *C07D 307/52* (2013.01)

(58) Field of Classification Search
CPC .. C07D 233/64; C07D 249/08; C07D 257/04; C07D 277/28; C07D 277/64; C07C 211/37; C07C 211/36; C07C 217/74; A61K 31/428; A61K 31/426; A61K 31/41; A61K 31/4196; A61K 31/417; A61K 31/131; A61K 31/138
See application file for complete search history.

(56) References Cited

U.S. PATENT DOCUMENTS

| | | | |
|---|---|---|---|
| 2009/0005456 A1 * | 1/2009 | Shao et al. .................... | 514/650 |
| 2014/0221473 A1 * | 8/2014 | Amin et al. .................... | 514/462 |

FOREIGN PATENT DOCUMENTS

| | | | |
|---|---|---|---|
| CN | 101308139 B | * | 12/2012 |
| WO | WO2006/048546 A1 | * | 5/2006 |

* cited by examiner

*Primary Examiner* — Joseph Kosack
*Assistant Examiner* — Amanda L Aguirre

(57) ABSTRACT

The invention is directed to a compound of formula I, as defined herein, or a pharmaceutically acceptable salt thereof; a pharmaceutical composition containing a compound of formula I, a method of treatment of a disorder or condition that may be treated by administration of the compound, the method comprising administering to a mammal, especially a human, in need of such treatment a compound of formula I as described above, and a method of treatment of a disorder or condition selected from the group consisting Human African Trypanosomiasis (HAT), Chagas Disease, Malaria, Leishmaniasis, and other infectious diseases transmitted to humans and animals by exposure to parasites, the method comprising administering to a human or mammal in need of such treatment a compound of formula I as described above.

14 Claims, No Drawings

CYCLOALKYL-DIAMINES

This application claims the benefit of U.S. Provisional Application Ser. No. 61/758,538 filed on Jan. 30, 2013.

BACKGROUND OF THE INVENTION

The present invention relates to novel cycloalkyl-diamines, pharmaceutical compositions comprising such compounds and the use of such compounds in the treatment and prevention of Human African Trypanosomiasis (HAT), Chagas Disease, Leishmaniasis, Malaria and similar parasitic diseases in humans and animals.

Human African Trypanosomiasis (HAT) is a disease spread by *trypanosoma brucei*, a parasitic organism which is transmitted to humans primarily via bites from the tsetse fly. HAT is often referred to as "sleeping sickness" because of the symptoms that emerge in patients who have progressed to the advanced, or Stage 2, level of infection following exposure to the CNS by the parasite; this latter stage of the disease is typically fatal (Jacobs and Ding, *Annual Reports in Medicinal Chemistry*, (2010), 45:277-294; Rollo, in *Goodman and Gilman's, The Pharmacological Basis of Therapeutics*, 12th Ed., (2011), 1419-1441).

The disease is found in two forms, depending on the causative parasite (*Trypanosoma brucei gambiense* or *Trypanosoma brucei rhodesiense*). *T. b. gambiense* is primarily found in central and western Africa and causes a chronic condition that can remain in a passive phase for months or years before symptoms emerge. *T. b. rhodesiense* is found in southern and eastern Africa; symptoms of infection generally emerge in a few weeks and are more virulent and faster developing than *T. b. gambiense*. Approximately one-half million inhabitants of sub-Saharan Africa are potentially infected each year by the hemolymphatic, Stage 1, form of HAT. Symptoms include fever, headaches, joint pain and itching, as well as severe swelling of lymph nodes; chronically HAT symptoms include anemia, endocrine, cardiac and kidney dysfunctions.

Nearly 10,000 deaths have been reported as recently as 2010 from neurological, or Stage 2, HAT (Simarro, *International Journal of Health Geographics*, (2010), 9:57). Symptoms for these patients are generally more severe, including confusion, reduced coordination and disruption of the sleep cycle, as well as progressive mental deterioration leading to coma and death. Damage as a result of Stage 2 HAT is irreversible.

During the past decade there has been a renewed interest in developing safer, more efficacious HAT drugs, with an increased recognition of the impact of this disease upon quality of life for patients and their society in general. In fact, little had been accomplished over the past three decades to identify and develop safer and more efficacious medications for HAT, particularly for patients suffering from the advanced stage of this disease. The drugs most commonly used are essentially antifungal compounds, acting directly on the invasive protozoa in the bloodstream; poor penetration of the blood-brain barrier (BBB) has limited the use of some of these drugs to treatment of the hemolymphatic first stage of HAT. The most commonly prescribed treatments include pentamidine, suramin, melarsoprol, eflornithine and the combination therapy NECT (nifurtimox plus eflornithine). However, a growing concern in recent years is the issue of cross-resistance to some of the currently available medications. This is especially the case with pentamidine and arsenicals like melarsoprol (see Koning, *Trends in Parasitology*, (2008), 24(8):345-349).

The organism responsible for HAT, *Trypansoma brucei* (*T. brucei*), is also related to other parasitic species which can cause severely debilitating symptoms in humans and animals. Chagas disease, for example, caused by the related parasite *Trypanosoma cruzi*, is prevalent in a number of South American countries, affecting as many as 10 million individuals. It has also been detected in cattle, causing financial hardship for ranches as well as individual herders. Fatalities from Chagas disease are estimated to be about 21,000 per year and usually involve cardiovascular damage leading to death for the most seriously infected patients. Leishmaniases, detected in several forms, are estimated to affect as many as two million people on four continents while malaria, spread by exposure to one or more *Plasmodium* organisms, continues to afflict humans throughout the world.

One of the most commonly used HAT treatments for Stage 1 exposure is pentamidine. This diamidine compound has been extensively studied with respect to structure-activity relative to the replacement of the 1,5-dioxopentyl portion of the molecule by a variety of aryl and heteroaryl rings (e.g., Tidwell (2006) *Journal of Medicinal Chemistry*, 49:5324). However, little has been done to enhance pentamidine's brain concentration, e.g., through the incorporation of functional groups associated with enhanced CNS-penetration, such as those found in the most effective antipsychotic and antidepressant drugs currently on the market. Thus, it is possible that new treatments which target the *T. brucei* parasite and HAT could demonstrate sufficient efficacy against these related parasitic organisms and would thus be of immense value as antiparasitic therapeutic agents (Silva (2007) *Biochemical Pharmacology* 73:1939-1946).

SUMMARY OF THE INVENTION

The present invention is directed to compounds of the formula I:

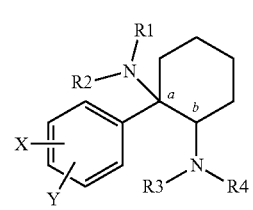

or the pharmaceutically acceptable salt(s) thereof, wherein:

X and Y are independently selected from the group consisting of H, F, Cl, Br, I, ON, OH, $CF_3$, $C_2F_5$, $C_1$-$C_6$-alkyl, $C_3$-$C_7$-cycloalkyl, $C_1$-$C_3$-alkoxy, aryl, heteroaryl, -(—C=O)—R5, —NH—(C=O)—R5, —NR5-(C=O)—R6, —(C=O)—NHR5 and —(C=O)—NR5R6[[.]];

R1 is hydrogen;

R2 is hydrogen or $C_1$-$C_6$-alkyl;

R3 is hydrogen or $C_1$-$C_6$-alkyl;

R4 is selected from the group consisting of $C_1$-$C_6$-alkyl, $C_3$-$C_7$-cycloalkyl, $(CH_2)_n$—R7, or NR3R4 is a 5- to 12-membered cyclic or bicyclic ring system containing up to two additional heteroatoms in the ring, selected from N, O and S;

R5 is selected from $C_1$-$C_6$-alkyl and aryl;

R6 is selected from $C_1$-$C_6$-alkyl and aryl, or

NR5R6 is a 5- to 12-membered cyclic or bicyclic ring system containing up to two additional heteroatoms in the ring, selected from N, O and S;

R7 is independently selected from the group consisting of H, $C_1$-$C_6$-alkyl, $C_3$-$C_7$-cycloalkyl, ($C_1$-$C_6$-alkyloxy)-, ($C_1$-$C_6$-alkyloxy)-($C_1$-$C_6$-alkyl)-, NR8R9-, NR8R9-($C_1$-$C_6$-alkyl), aryl, heterocyclyl and heteroaryl; and R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S; and n is an integer between 0 and 6.

The invention is also directed to a pharmaceutical composition for treating a disorder or condition selected from the group consisting of HAT, Chagas disease, Leishmaniasis in a mammal, including a human, that may be treated by administering to a mammal in need of such treatment a compound of formula I as described above, or a pharmaceutically acceptable salt thereof, that is effective in treating such disorder or condition, and a pharmaceutically acceptable carrier.

The invention is also directed to a method of treatment of a disorder or condition selected from the group consisting of the disorders or conditions listed in the previous paragraph (e.g., HAT, Chagas disease, Leishmaniasis, Malaria), the method comprising administering to said mammal in need of such treatment an amount of a compound of formula I as described above that is effective in treating such disorder or condition.

Preferred embodiments of the present invention include the compounds of formula I in which:

(A) R2 is methyl, R1 and R3 are hydrogen, Y is hydrogen; X is halogen;
n is an integer between 0 and 6; and
R7 is cycloalkyl.

(B) R2 is methyl, R1 and R3 are hydrogen, Y is hydrogen; X is halogen;
n is an integer between 0 and 6; and
R7 is —($C_1$-$C_3$)-alkoxy.

(C) R2 is methyl, R1 and R3 are hydrogen, and Y is hydrogen;
X is halogen:
n is an integer between 0 and 6; and
R7 is aryl or heteroaryl.

(D) R2 is methyl, R1 and R3 are hydrogen; Y is hydrogen; X is halogen;
n is an integer between 0 and 6; and
R7 is heterocyclyl.

(E) R2 is methyl; R1 and R3 are hydrogen; Y is hydrogen; X is halogen;
n is an integer between 0 and 6; and
R7 is NR8R9.

The most preferred embodiment of the present invention includes the compounds of formula I in which:
NR1R2 and NR3R4 groups at positions "a" and "b" are oriented cis to each other,
X is 2-chloro;
Y is hydrogen;
R1 is hydrogen;
R2 is methyl; and
R3 is hydrogen.

Preferred compounds of formula I in accordance with the present invention are the following:
Trans-1-(2-chlorophenyl)-$N^2$-(2-(dimethylamino)ethyl)-$N^1$-methylcyclohexane-1,2-diamine;
Cis-1-(2-chlorophenyl)-$N^2$-(2-(dimethylamino)ethyl)-$N^1$-methylcyclohexane-1,2-diamine;
Trans-1-(2-chlorophenyl)-$N^2$-cyclopoppyl-$N^1$-methylcyclohexane-1,2-diamine;
Cis-1-(2-chlorophenyl)-$N^2$-cyclopropy-$N^1$-methylcyclohexane-1,2-diamine;
Trans-1-(2-chlorophenyl)-$N^2$-cyclopentyl-$N^1$-methylcyclohexane-1,2-diamine;
Cis-1-(2-chlorophenyl)-$N^2$-cyclopentyl-$N^1$-methylcyclohexane-1,2-diamine;
Trans-1-(2-chlorophenyl)-$N^2$-(3-methoxypropyl)-$N^1$-methylcyclohexane-1,2-diamine;
Cis-1-(2-chlorophenyl)-$N^2$-(3-methoxypropyl)-$N^1$-methylcyclohexane-1,2-diamine;
Trans-1-(2-chlorophenyl)-$N^1$-methyl-$N^2$-(tetrahydrofuran-2-ylmethyl)cyclohexane-1,2-diamine;
Cis-1-(2-chlorophenyl)-$N^1$-methyl-$N^2$-(tetrahydrofuran-2-ylmethyl)cyclohexane-1,2-diamine;
Cis-1-(2-chloropheny)-$N^2$-(3-(dimethylamino)propyl)-$N^1$-methylcyclohexane-1,2-diamine;
Trans-$N^2$-benzyl-1-(2-chlorophenyl)-$N^1$-methylcyclohexane-1,2-diamine;
Cis-$N^2$-benzyl-1-(2-chlorophenyl)-$N^1$-methylcyclohexane-1,2-diamine;
Cis-1-(2-chlorophenyl)-$N^1$-methyl-$N^2$-(pyridin-4-ylmethyl)cyclohexane-1,2-diamine;
Trans-1-(2-chlorophenyl)-$N^1$-methyl-$N^2$-(pyridin-3-ylmethyl)cyclohexane-1,2-diamine;
Cis-1-(2-chlorophenyl)-$N^2$-(1-(R)-phenyl)-ethyl)-$N^1$-methylcyclohexane-1,2-diamine;
Trans-1-(2-chlorophenyl)-$N^2$-(1-(S)-phenyl)-ethyl)-$N^1$-methylcyclohexane-1,2-diamine;
Trans-1-(2-chlorophenyl)-$N^2$-(3-(1-imidazolyl)-propyl)-$N^1$-methylcyclohexane-1,2-diamine;
Cis-1-(2-chlorophenyl)-$N^2$-(3-(1-imidazolyl)-propyl)-$N^1$-methylcyclohexane-1,2-diamine;
Trans-1-(2-chlorophenyl)-$N^2$-(1-ethyl-pyrrolidin-2-ylmethyl)-$N^1$-methylcyclohexane-1,2-diamine;
Cis-1-(2-chlorophenyl)-$N^2$-(1-ethyl-pyrrolidin-2-ylmethyl)-$N^1$-methylcyclohexane-1,2-diamine;
Trans-1-(2-chlorophenyl)-$N^2$-(3-(pyrrolidin-1-yl)propyl)-$N^1$-methylcyclohexane-1,2-diamine;
Cis-1-(2-chlorophenyl)-$N^2$-(3-(pyrrolidin-1-yl)propyl)-$N^1$-methylcyclohexane-1,2-diamine;
Trans-1-(2-chlorophenyl)-$N^2$-(3-phenylpropyl)-$N^1$-methylcyclohexane-1,2-diamine;
Cis-1-(2-chlorophenyl)-$N^2$-(3-phenylpropyl)-$N^1$-methylcyclohexane-1,2-diamine;
Trans-1-(2-chlorophenyl)-$N^2$-(3-(morpholin-1-yl)propyl)-$N^1$-methylcyclohexane-1,2-diamine;
Cis-1-(2-chlorophenyl)-$N^2$-(3-(morpholin-1-yl)propyl)-$N^1$-methylcyclohexane-1,2-diamine;
Trans-1-(2-chlorophenyl)-$N^2$-(3-(4-methylpiperazin-1-yl)propyl)-$N^1$-methylcyclohexane-1,2-diamine;
Cis-1-(2-chlorophenyl)-$N^2$-(3-(4-methylpiperazin-1-yl)propyl)-$N^1$-methylcyclohexane-1,2-diamine;
Trans-1-(2-chlorophenyl)-$N^2$-cyclohexyl-$N^1$-methylcyclohexane-1,2-diamine; and Cis-1-(2-chlorophenyl)-$N^2$-cyclohexyl-$N^1$-methylcyclohexane-1,2-diamine.

Other compounds of the invention include the following:
1-(2-chloro-4-methoxyphenyl)-$N^2$-[3-(4,5-dimethyl-1H-imidazol-2-yl)propyl]-$N^1$-methyl-cyclohexane-1,2-diamine;
1-(2-chlorophenyl)-$N^1$-methyl-$N^2$-[3-(1H-1,2,4-triazol-5-yl)propyl]-cyclohexane-1,2-diamine;
1-(2-methylphenyl)-$N^1$-methyl-$N^2$-[3-(3-methyl-1H-1,2,4-triazol-5-yl)propyl]-cyclohexane-1,2-diamine;
1-(2,4-dichlorophenyl)-$N^1$-methyl-$N^2$-[3-(1H-tetrazol-5-yl)propyl]-cyclohexane-1,2-diamine;
1-(3,4-fluorophenyl)-$N^1$-methyl-$N^2$-[2-(1-methyl-1H-tetrazol-5-yl)ethyl]-cyclohexane-1,2-diamine;

1-(4-chlorophenyl)-$N^2$-(2-(dimethylamino)ethyl)-$N^1$-methylcyclohexane-1,2-diamine;
1-(2,4-dichlorophenyl)-$N^2$-(2-(dimethylamino)ethyl)-$N^1$-methylcyclohexane-1,2-diamine;
1-(3,4-difluorophenyl)-$N^2$-(2-(dimethylamino)ethyl)-$N^1$-methylcyclohexane-1,2-diamine;
1-(4-isopropylphenyl)-$N^2$-(2-(dimethylamino)ethyl)-$N^1$-methylcyclohexane-1,2-diamine;
1-(2-methoxyphenyl)-$N^2$-(2-(dimethylamino)ethyl)-$N^1$-methylcyclohexane-1,2-diamine;
1-(2-chlorophenyl)-$N^2$-(2-(dimethylamino)ethyl)-$N^1$-methylcyclohexane-1,2-diamine;
1-(2-chlorophenyl)-$N^2$-[3-(1H-imidazol-2-yl)propyl]-$N^1$-methylcyclohexane-1,2-diamine;
1-(2-chlorophenyl)-$N^2$-[2-(1H-imidazol-2-yl)ethyl]-$N^1$-methylcyclohexane-1,2-diamine;
1-(2-chlorophenyl)-$N^1$-methyl-$N^2$-[3-(1,3-thiazol-2-yl)propyl]-cyclohexane-1,2-diamine;
1-(3,5-dimethyl-2-chlorophenyl)-$N^1$-methyl-$N^2$-[3-(1,3-thiazol-2-yl)propyl]-cyclohexane-1,2-diamine;
1-(3,5-dimethyl-phenyl)-$N^1$-methyl-$N^2$-[3-(4,5-dimethyl-1,3-thiazol-2-yl)propyl]-cyclohexane-1,2-diamine;
1-(2-chlorophenyl)-$N^2$-[3-(1,3-benzothiazol-2-yl)propyl]-$N^1$-methylcyclohexane-1,2-diamine;
1-(2,3-dichlorophenyl)-$N^2$-[3-(1,3-benzimidazol-2-yl)propyl]-$N^1$-methylcyclohexane-1,2-diamine;
1-(3,4-dichlorophenyl)-$N^2$-(2-(3,4-difluorophenyl)ethyl)-$N^1$-methylcyclohexane-1,2-diamine;
1-(2-chlorophenyl)-$N^2$-[(4,5-dimethyl-1H-imidazol-2-yl)methyl]-$N^1$-ethylcyclohexane-1,2-diamine; and
1-(2-chlorophenyl)-$N^1$-ethyl-$N^2$-[(1-methyl-1H-imidazol-2-yl)methyl]cyclohexane-1,2-diamine.

DETAILED DESCRIPTION OF THE INVENTION

The compounds of formula I may be prepared as described in the following reaction schemes and discussions. Unless otherwise indicated, X, Y, R1, R2, R3, R4, R5, R6, R7 and structural formulae II, III, IV, V, VI, VII, VIII, IX, X, XI, XII, XIII, XIV and XV in the reaction schemes and discussion that follow are defined as above.

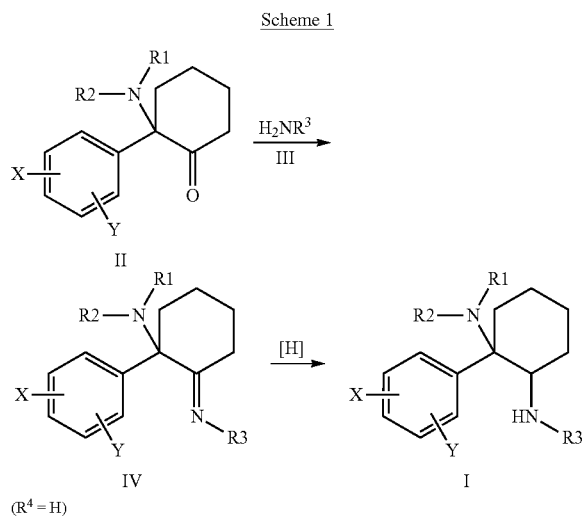

According to Scheme 1, a ketone of the general formula II, wherein X, Y, $R^1$ and $R^2$ are as previously defined, may be converted directly into the corresponding compound of the formula I, via an intermediate of the general formula IV, by reacting it with one or more equivalents of an primary amine of the general formula III in the presence of a reducing reagent. Reducing reagents that may be used include sodium cyanoborohydride, sodium triacetoxyborohydride, sodium borohydride, lithium aluminum hydride, hydrogen plus a metal catalyst, zinc plus hydrochloric acid, and formic acid. This reaction is typically conducted in a reaction inert solvent at a temperature from about 0° C. to about 150° C., but may be conducted in the absence of solvent. Suitable reaction inert solvents include lower alcohols (e.g., methanol, ethanol, isopropanol), 1,2-dichloroethane, acetic acid and tetrahydrofuran (THF)). Preferably the reaction is conducted with an excess of the corresponding amine III, in the absence of additional solvent, at a temperature of about 110° C., and using the reducing agent sodium cyanoborohydride.

Alternatively, the reaction of a compound of formula II with an amine compound of the formula III may be carried out in the presence of a dehydrating agent (e.g., titanium tetrachloride) or by using an apparatus designed to azeotropically remove the water generated, to produce an imine of the formula IV. This imine may then be converted to the title product of formula I by reduction of the C=N bond with a reducing agent as described above, preferably with sodium cyanoborohydride in the presence or absence of a suitable, reaction inert solvent as described in the preceding paragraph at a temperature of about 0° C. to about 150° C. and preferably at about 110° C. Other suitable dehydrating agents/solvent systems include titanium tetrachloride in dichloromethane, titanium isopropoxide in dichloromethane and activated molecular sieves in toluene or in dichloromethane.

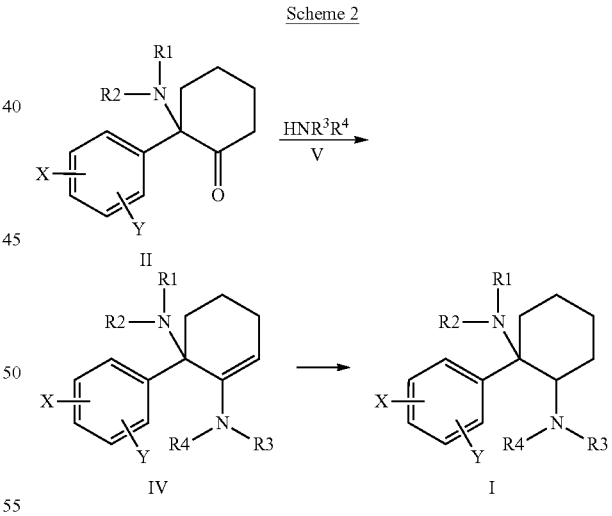

When a secondary amine of the general formula V (i.e., HNR3R4) is used, an alternative method involves the formation of an enamine of general formula VI, which can be reduced to the title product of formula I through the use of a selective reducing agent or selective reduction conditions known to one familiar with the art of organic synthesis. Using this procedure, as shown in Scheme 2 above, the intermediate enamine VI may be isolated and purified if it is stable, or it may be used directly in the reduction step to generate the diamine of general formula I. Selective reducing agents and reagents to facilitate the conversion of intermediate VI to the compounds of formula I include: formic acid, hydrogen gas and a metal catalyst (e.g., Pd on carbon, Pt on carbon).

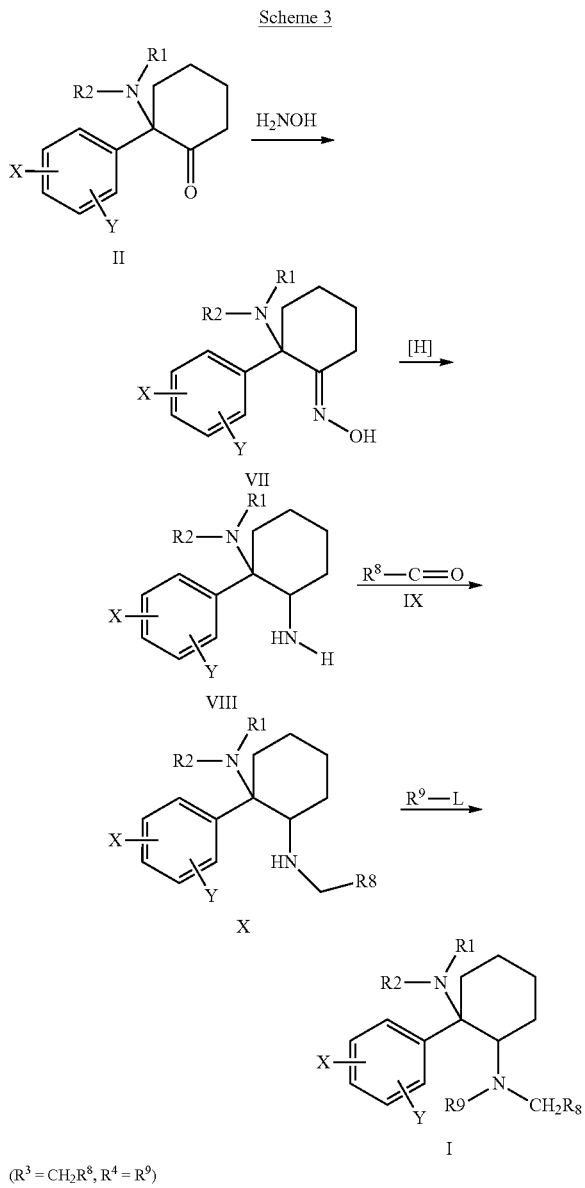

(R3 = CH2R8, R4 = R9).

In another method (Scheme 3) for the preparation of the compounds of the present invention, an intermediate oxime (VII) can be prepared through reaction of the starting ketone I and hydroxylamine. Synthesis of such oximes is well precedented in the chemical literature (e.g., see LaMattina, J L (*Synthesis* (1980) 329-330), and it is also known that intermediate oximes like VII are capable of forming two different isomers, denoted as Z- and E-oximes. These isomers may or may not react differently in their subsequent conversion to intermediates of general formulae VIII (i.e., I, R3, R4=H), and one of the oxime isomers may be less reactive or resistant to reduction to intermediate VIII. The reduction to VIII can be achieved using one of a variety of reagents and procedures, including Zn—AcOH, Na and $C_2H_5OH$, $BH_3$, and $NaBH_3CN$—$TiCl_3$.

In the next step, compound VIII can be converted to a compound of general formula X by subjecting it to a reductive amination with an aldehyde of general formula IX (for examples, see Jerry March, "Advanced Organic Chemistry: Reactions, Mechanisms and Structure",4$^{th}$ Ed., John Wiley & Sons, New York, N.Y. (1992) pp 898-900) followed by alkylation of the nitrogen atom of the intermediate of general formula X with a reagent of general formula R9-L, where L is a leaving group (e.g., Cl, Br, mesylate) and R9 is $C_1$-$C_3$ alkyl. Procedures for these reactions are readily available in the chemical literature and familiar to chemists with skill in the art of organic synthesis.

The starting ketone for the above processes, compound II, may be obtained from commercial sources or may be synthesized as described in the chemical literature (Scheme 4). Such compounds may exist as racemic mixtures or as the individual (+)- and (−)-isomers.

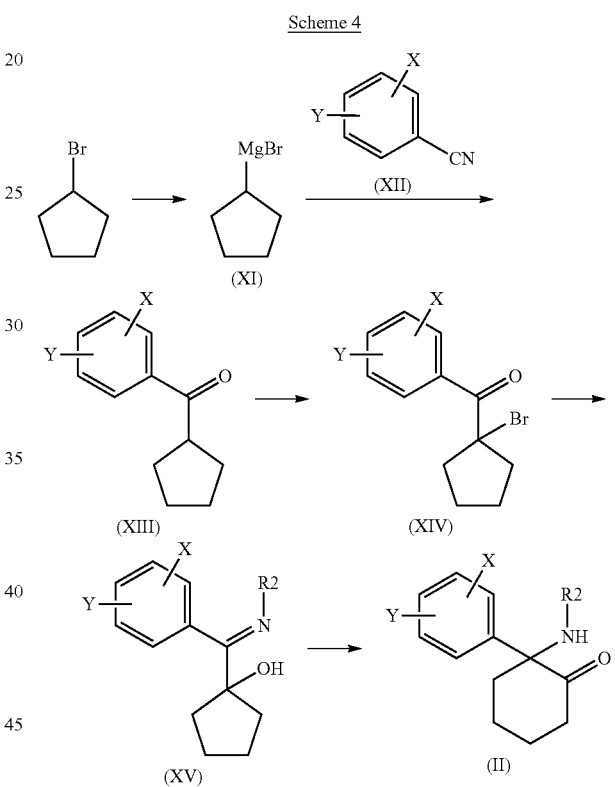

In general, 1-bromo-cyclopentane is converted to a Grignard reagent (XI) by reaction with magnesium metal in an inert solvent, typically in ethers like diethyl ether or tetrahydrofuran (THF). The Grignard reagent so formed is then reacted with an appropriately substituted arylnitrile (XII), in an inert solvent such as hexane, and stirred at room temperature until the reaction is determined to have been completed. The product, arylketone (XIII), dissolved in a suitable solvent (e.g., chloroform) is then treated with one equivalent of bromine ($Br_2$), and the resulting α-bromo-ketone (XIV) is isolated by filtration. Compound XIV is then added to a primary amine of general formula R2-$NH_2$ in an inert solvent (e.g., toluene) and the mixture is heated to reflux. The solvents are subsequently removed under vacuum to obtain the crude α-hydroxy-imine (XV). This intermediate is then heated, typically in a high-boiling, inert solvent (e.g., decalin) wherein the compound undergoes a thermal rearrangement to produce the α-amino-ketone (II).

Specifically, the compound II in which X is 2-chloro, Y is H, R1 is hydrogen and R2 is methyl is commonly referred to as ketamine. Ketamine is a Central Nervous System active drug that may interact with NMDA (i.e., N-Methyl-D-Aspartate) receptors in the brain and has been associated with a variety of behavioral disorders in human and animal studies. The synthesis and utility of ketamine and related analogs as NMDA receptor modulators and disease treatments are described by T. G. Gant and S. Sarshar in US Patent Application 2008/109958 (Apr. 25, 2008).

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate.

Where cis- and trans-isomers are possible (i.e., at positions "a" and "b" in structure formula I), for an embodiment of the inventive compounds of formula I, both cis- and trans-isomers (i.e., diastereomers) are within the scope of this invention.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2$H, $^3$H, $^{11}$C, $^{13}$C, $^{13}$N, $^{15}$N, $^{18}$O, $^{35}$S, $^{31}$P, $^{33}$P, $^{18}$F and $^{37}$Cl, respectively.

Compounds of the present invention, prodrugs thereof, and pharmaceutically acceptable salts of said compounds, or of said prodrugs which contain the aforementioned isotopes and/or other isotopes of other atoms are within the scope of this invention. Certain isotopically labeled compounds of the present invention, for example, those into which radioactive isotopes such as $^3$H and 14C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydro-naphthalinyl (i.e., tetralinyl), indenyl, and the like.

The term "halogen" represents chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-member rings that contain from one to three heteroatoms independently selected from oxygen, nitrogen, and sulfur. Examples of preferred heteroaryl groups include, but are not limited to, benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl, pyridinyl, triazolyl, tetrazolyl and the like.

The invention is further directed to a pharmaceutical composition for treating, for example, human African Trypanosomiasis (HAT), Chagas Disease, Leishmaniasis, Malaria and similar diseases in humans and animals transmitted by parasites.

The invention is also directed to a method of treatment of infectious diseases including, but not limited to, human African Trypanosomiasis (HAT), Chagas Disease, Leishmaniasis, Malaria, and similar diseases in humans and animals transmitted by parasites.

The pharmaceutical composition and method of this invention may also be used for preventing a relapse in a disorder or condition described in the preceding paragraphs. Preventing such relapse is accomplished by administering to a mammal in need of such prevention a compound of formula I as described above.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buckle, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichloro-fluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., HAT) is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially brought under control. Lower doses given less frequently can be used prophylactically to prevent or reduce the incidence of recurrence of the infection.

Aerosol formulations for treatment of the conditions referred to above (e.g. HAT) in the average human are preferably arranged such that each metered dose or "puff" of aerosol contains 0.1 micrograms to 100 micrograms of the active compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

Examples of the disorders or conditions which may be treated by the compound, composition and method of this invention include: human African Trypanosomiasis (HAT), Chagas Disease, Leishmaniasis, Malaria, and similar diseases in humans and animals transmitted by parasites.

As an example, the mammal in need of treatment or prevention may be a human. As another example, the mammal in need of treatment or prevention may be a mammal other than a human.

A compound of formula I which is basic in nature is capable of forming a wide variety of different salts with various inorganic and organic acids. The acid additions salts are readily prepared by treating the base compounds with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used in this document are intended to have the following, general meaning:

bm: broad multiplet (NMR)
bs: broad singlet (NMR)
d: doublet (NMR)
dd: doublet of doublets (NMR)
d.e.: diatomaceous earth, filtering agent
calcd.: calculated value
J: coupling constant (NMR)
LC: high pressure liquid chromatography (HPLC)

m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged to be homogeneous by thin layer chromatography and NMR. Thin layer chromatography was performed on Kieselgel plates eluting with the indicated solvents, visualized by using a 254 nm UV lamp, and stained with either an aqueous $KMnO_4$ solution or an ethanolic solution of 12-molybdophosphoric acid.

Nuclear Magnetic Resonance (NMR) spectra were acquired on a 400 MHz NMR Spectrometer. Chemical shifts for proton $^1$H-NMR spectra are reported in parts per million (ppm) relative to the singlet of $CDC_3$ at 7.24 ppm.

Preparative conditions for Chromatographic Purification and Analysis.

Instrument:
LaChrom HPLC system (Merck-Hitachi) for UV-directed purification and Waters HPLC/MS for mass directed purification, both equipped with RP $C_{18}$ column (Phenomenex Gemini NX 5µ 150 mm×30 mm).

Eluent I:
A: Acetonitrile-$H_2O$=5:95, 10 mM $NH_4HCO_3$ buffer, pH 8.0
B: Acetonitrile-$H_2O$=80:20 10 mM $NH_4HCO_3$ buffer, pH 8.0

Eluent II:
A: Acetonitrile-$H_2O$=5:95, 20 mM $HCOONH_4/NH_4OH$ buffer, pH 7.4
B: Acetonitrile-$H_2O$=80:20, 20 mM $HCOONH_4/NH_4OH$ buffer, pH 7.4

Eluent III:
A: Acetonitrile-$H_2O$=5:95, 20 mM $CH_3COONH_4/CH_3COOH$ buffer, pH 6
B: Acetonitrile-$H_2O$=80:20, 20 mM $CH_3COONH_4/CH_3COOH$ buffer, pH 6

Eluent IV:
A: $H_2O$ with 0.1% TFA, pH 2.2
B: Acetonitrile with 0.1% TFA, pH 2.2

Gradient program: adjusted according to the compound properties
Column Temp.: room temperature (25° C.)
Flow Rate: up to 40 ml/min
Detection and triggering: UV detector (220 nm)
Conditions for LC-MS analysis:
Column:
Zorbax RRHD Eclipse XDB (Agilent) $C_{18}$, 1.9 micron, 50 mm×2.1 mm.

Eluent I:
A: Acetonitrile-$H_2O$=5:95, 20 mM $HCOONH_4/NH_4OH$ buffer, pH 7.4
B: Acetonitrile-$H_2O$=80:20, 20 mM $HCOONH_4/NH_4OH$ buffer, pH 7.4

Eluent I:
A: $H_2O$ with 0.1% TFA, pH 2.2
B: Acetonitrile with 0.1% TFA, pH 2.2

Gradient program: adjusted according to the compound properties; typically, start: 0% B to 100% B in 1 minute, 0.8 minute isocratic B.
Column Temp.: 40° C.
Flow Rate: 0.6 mL/min
Sample Conc.: ca. 1 mg/mL
Sample Solvent: Acetonitrile
Injection: 0.5 µL
Detection wavelength: 220 nm
MS Conditions:
Measured Mass Range: 100-750 Daltons
Scan Time: 0.2 s
Ion mode: ES±
Cone Voltage: 20 V
Capillary Voltage: 3 V
Source temp.: 140° C.
Desolvation temp.: 450° C.
Desolvation gas: 450 L/h
Cone gas: 60 L/h Example 1

General Procedure A

Trans-1-(2-chlorophenyl)-$N^2$-(2-(dimethylamino) ethyl)-$N^1$-methylcyclohexane-1,2-diamine (1a) and Cis-1-(2-chlorophenyl)-$N^2$-(2-(dimethylamino) ethyl)-$N^1$-methylcyclohexane-1,2-diamine (1b)

A mixture of 2-(2-chlorophenyl)-2-(methylamino)cyclohexanone hydrochloride (ketamine HCl) (423 mg, 1.54 mmol) and $N^1$,N-dimethylethane-1,2-diamine (1.6 mL, 19.2 mmol) was heated at 110° C. for 20 h. The mixture was cooled to room temperature and sodium cyanoborohydride (490 mg, 7.8 mmol) was added. The mixture was then heated at 110° C. overnight. The cooled reaction mixture was quenched with saturated $NaHCO_3$, extracted with $CH_2Cl_2$ (75 mL), dried ($Na_2SO_4$) and concentrated to dryness to give 500 mg of crude product (M/Z 310 [M$^+$+H]). This material was further purified by column chromatography, as described in Method A above.

a.) The product fractions, (RT=0.50) were combined, the solvents were removed and the trans-isomer was isolated as a trifluoroacetate salt, 0.149 g.

MS: calcd. for $C_{17}H_{28}ClN_3$: 309.9; obsd.: 309.2 (m+1).

$^1$H-nmr (DMSO-$d_6$, 400 MHz, T=30° C.) δ 1.4-1.7 (m, 3H), 1.75-2.0 (m, 3H), 2.10-2.35 (m+s, 5H), 2.40-2.50 (m+s, 6H), 2.75-2.85 (m, 2H), 2.92 (m, 1H), 3.15 (m, 1H), 7.40-7.50 (m, 2H), 7.55-7.65 (m, 2H), 8.5 (bs, 1H).

b.) The more polar fractions (RT=0.64) were separately combined and, after removal of the solvents, the cis-isomer was isolated as a solid, 0.078 g.

MS: calcd. for $C_{17}H_{28}ClN_3$: 309.9; obsd.: 309.19 (m+1).

The following compounds were also prepared using the general procedure A, as described above for the title compounds of Examples 1:

Example 2

Trans-1-(2-chlorophenyl)-$N^2$-cyclopropylmethyl-$N^1$-methylcyclohexane-1,2-diamine (2a), and Cis-1-(2-chlorophenyl)-$N^2$-cyclopropylmethyl-$N^1$-methylcyclohexane-1,2-diamine (2b)

The title compounds of Example 2 were prepared according to general procedure A using cyclopropylmethanamine and ketamine.

a.) LC (RT=0.55)/Mass spectrum (m/z) calcd. for $C_{17}H_{25}ClN_2$: 292.8; obsd.: 293 (M+1, 100%), 295 (M+1, 37Cl, 30%), 262 (28%).

$^1$H-nmr (DMSO-$d_6$, 400 MHz, T=30° C.) δ 0.1 (m, 2H), 0.2 (m, 2H), 0.5 (m, 2H), 0.85 (m, 1H), 1.50 (m, 2H), 1.65 (d, 1H), 1.85-2.10 (m, 2H), 2.05 (s, 3H), 2.15 (m, 2H), 2.30-2.55 (m, 2H), 2.70 (dd, 1H), 4.45 (s, 1H), 7.40-7.65 (m, 4H).

b.) LC (RT=0.72)/MS: calcd. for $C_{17}H_{25}ClN_2$: 292.8; obsd.: 293 (M+1).

$^1$H-nmr (DMSO-$d_6$, 400 MHz, T=30° C.) δ 0.30 (m, 2H), 0.55 (dd, 2H), 1.0 (m, 1H), 1.2 (m, 1H), 1.40-1.85 (m, 5H), 2.05 (m+s, 4H), 2.80 (m, 3H), 4.20 (m, 1H), 6.5 (bs, 2H), 7.35-7.50 (m, 2H), 7.52 (dd, 1H), 7.64 (d, 1H).

Example 3

Trans-1-(2-chlorophenyl)-N$^2$-cyclopentyl-N$^1$-methylcyclohexane-1,2-diamine (3a), and Cis-1-(2-chlorophenyl)-N$^2$-cyclopentyl-N$^1$-methylcyclohexane-1,2-diamine (3b)

The title compounds of Example 3 were prepared according to general procedure A using cyclopentylamine and ketamine.

a.) LC (RT=0.58)/MS: calcd. for $C_{18}H_{27}ClN_2$: 306.9; obsd.: 306.19 (m+1).

b.) LC (RT=0.96)/MS: calcd. for $C_{18}H_{27}ClN_2$: 306.9; obsd.: 306.19 (m+1).

Example 4

Trans-1-(2-chlorophenyl)-N$^2$-(3-methoxypropyl)-N$^1$-methylcyclohexane-1,2-diamine (4a), and Cis-1-(2-chlorophenyl)-N$^2$-(3-methoxypropyl)-N$^1$-methylcyclohexane-1,2-diamine (4b)

The title compounds of Example 4 were prepared according to general procedure A using 3-methoxypropylamine and ketamine.

a.) LC (RT=0.59)/MS: calcd. for $C_{17}H_{27}ClN_2O$: 310.9; obsd.: 310.18 (m+1).

b.) LC (RT=0.67)/MS: calcd. for $C_{17}H_{27}ClN_2O$: 310.9; obsd.: 310.18 (m+1).

Example 5

Trans-1-(2-chlorophenyl)-N$^1$-methyl-N$^2$-(tetrahydrofuran-2-ylmethyl)cyclohexane-1,2-diamine (5a), and Cis-1-(2-chlorophenyl)-N$^1$-methyl-N$^2$-(tetrahydrofuran-2-ylmethyl)cyclohexane-1,2-diamine (5b)

The title compounds of Example 5 were prepared according to general procedure A using 2-aminomethyl-2,3,4,5-tetrahydrofuran and ketamine.

a.) LC (RT=0.63)/MS: calcd. for $C_{18}H_{27}ClN_2O$: 322.9; obsd.: 322.18 (m+1).

b.) LC (RT=0.70)/MS: calcd. for $C_{18}H_{27}ClN_2O$: 322.9; obsd.: 322.18 (m+1).

Example 6

Cis-1-(2-chloropheny)-N$^2$-(3-(dimethylamino)propyl)N$^1$-methyl-cyclohexane-1,2-diamine (6)

The title compound of Example 6 was prepared according to general procedure A using 3-(N,N-dimethylamino)-propylamine and ketamine.

LC (RT=0.66)/MS: calcd. for $C_{18}H_{30}ClN_3$: 323.9; obsd.: 323.21 (m+1).

Example 7

Trans-N$^2$-benzyl-1-(2-chlorophenyl)-N$^1$-methylcyclohexane-1,2-diamine (7a) and Cis-N$^2$-benzyl-1-(2-chlorophenyl)-N$^1$-methylcyclohexane-1,2-diamine (7b)

The title compounds of Example 7 were prepared according to general procedure A using benzylamine and ketamine.

a.) LC (RT=0.66)/MS: calcd. for $C_{20}H_{25}ClN_2$: 328.9; obsd.: 328.17 (m+1).

b.) LC (RT=1.01)/MS: calcd. for $C_{20}H_{25}ClN_2$: 328.9; obsd.: 328.17 (m+1).

Example 8

Cis-1-(2-chlorophenyl)-N$^1$-methyl-N$^2$-(pyridin-4-ylmethyl)cyclohexane-1,2-diamine (8)

The title compound of Example 8 was prepared according to general procedure A using 4-(aminomethyl)-pyridine and ketamine.

LC (RT=0.70)/MS: calcd. for $C_{19}H_{24}ClN_3$: 329.9; obsd.: 329.17 (m+1).

Example 9

Trans-1-(2-chlorophenyl)-N$^1$-methyl-N$^2$-(pyridin-3-ylmethyl)cyclohexane-1,2-diamine (9)

The title compound of Example 9 was prepared according to general procedure A using 3-(aminomethyl)-pyridine and ketamine.

LC (RT=0.56)/MS: calcd. for $C_{19}H_{23}ClN_3$: 329.9; obsd.: 329.17 (m+1).

Example 10

Cis-1-(2-chlorophenyl)-N$^2$-(1-(R)-phenyl)-ethyl)-N$^1$-methylcyclohexane-1,2-diamine (10)

The title compound of Example 10 was prepared according to general procedure A using (R)-α-methyl-benzylamine and ketamine.

LC (RT=1.05)/MS: calcd. for $C_{21}H_{27}ClN_2$: 342.9; obsd.: 342.19 (m+1).

Example 11

Trans-1-(2-chlorophenyl)-N$^2$-(1-(S)-phenyl)-ethyl)-N$^1$-methylcyclohexane-1,2-diamine (11)

The title compound of Example 11 was prepared according to general procedure A using (S)-α-methyl-benzylamine and ketamine.

LC (RT=0.81)/MS: calcd. for $C_{21}H_{27}ClN_2$: 342.9; obsd.: 342.19 (m+1).

Example 12

Trans-1-(2-chlorophenyl)-N$^2$-(3-(1-imidazolyl)-propyl)-N$^1$-methylcyclohexane-1,2-diamine (12a), and Cis-1-(2-chlorophenyl)-N$^2$-(3-(1-imidazolyl)-propyl)-N$^1$-methylcyclohexane-1,2-diamine (12b)

The title compounds of Example 12 were prepared according to general procedure A using 3-(1-imidazolyl)-propylamine and ketamine.

a.) LC (RT=0.70)/MS: calcd. for $C_{19}H_{27}ClN_4$: 346.9; obsd.: 346.19 (m+1).
$^1$H-nmr (DMSO-d6, 400 MHz, T=30° C.) δ 1.35-1.55 (m, 2H), 1.60-1.75 (m, 1H), 1.80-2.00 (m, 4H), 2.05-2.35 (m+s, 6H), 2.45-2.70 (m, 2H), 3.95-4.25 (m, 3H), 7.40-7.50 (m, 3H), 7.55 (m, 1H), 7.60 (m, 1H), 7.70 (s, 1H), 8.95 (s, 1H).
b.) LC (RT=0.54)/MS: calcd. for $C_{19}H_{27}ClN_4$: 346.9; obsd.: 346.19 (m+1).
$^1$H-nmr (DMSO-d6, 400 MHz, T=30° C.) δ 1.25 (bs, 1H), 1.40 (bs, 1H), 1.50-1.80 (m, 4H), 1.90 (m, 1H), 2.00-2.25 (m+s, 5H), 2.55 (m, 1H), 2.70-2.95 (m, 2H), 3.90 (bs, 1H), 4.20-4.35 (m, 2H), 6.50 (bs, 2H), 7.40-7.45 (m, 2H), 7.52 (m, 1H), 7.65 (m, 1H), 7.70 (m, 1H), 7.75 (m, 1H), 9.10 (s, 1H).

Example 13

Trans-1-(2-chlorophenyl)-N$^2$-(1-ethyl-pyrrolidin-2-ylmethyl)-N$^1$-methylcyclohexane-1,2-diamine (13a), and Cis-1-(2-chlorophenyl)-N$^2$-(1-ethyl-pyrrolidin-2-ylmethyl)-N$^1$-methylcyclohexane-1,2-diamine (13b)

The title compounds of Example 13 were prepared according to general procedure A using N-ethyl-2-(aminomethyl)-pyrrolidine and ketamine.

a.) LC (RT=0.55)/MS: calcd. for $C_{20}H_{32}ClN_3$: 349.9; obsd.: 349.23 (m+1).
b.) LC (RT=0.70)/MS: calcd. for $C_{20}H_{32}ClN_3$: 349.9; obsd.: 349.23 (m+1).

Example 14

Trans-1-(2-chlorophenyl)-N$^2$-(3-(pyrrolidin-1-yl)propyl)-N$^1$-methylcyclohexane-1,2-diamine (14a), and Cis-1-(2-chlorophenyl)-N$^2$-(3-(pyrrolidin-1-yl)propyl)-N$^1$-methylcyclohexane-1,2-diamine (14b)

The title compounds of Example 14 were prepared according to general procedure A using N-(3-aminopropyl)-pyrrolidine and ketamine.

a.) LC (RT=0.50)/MS: calcd. for $C_{20}H_{32}ClN_3$: 349.9; obsd.: 349.23 (m+1).
b.) LC (RT=0.68)/MS: calcd. for $C_{20}H_{32}ClN_3$: 349.9; obsd.: 349.23 (m+1).

Example 15

Trans-1-(2-chlorophenyl)-N$^2$-(3-phenylpropyl)-N$^1$-methylcyclohexane-1,2-diamine (15a), and Cis-1-(2-chlorophenyl)-N$^2$-(3-phenylpropyl)-N$^1$-methylcyclohexane-1,2-diamine (15b)

The title compounds of Example 15 were prepared according to general procedure A using 3-aminopropylbenzene and ketamine.

a.) LC (RT=0.71)/MS: calcd. for $C_{22}H_{29}ClN_2$: 356.9; obsd.: 356.19 (m+1).
b.) LC (RT=0.77)/MS: calcd. for $C_{22}H_{29}ClN_2$: 356.9; obsd.: 356.19 (m+1).

Example 16

Trans-1-(2-chlorophenyl)-N$^2$-(3-(morpholin-1-yl)propyl)-N$^1$-methylcyclohexane-1,2-diamine (16a), and Cis-1-(2-chlorophenyl)-N$^2$-(3-(morpholin-1-yl)propyl)-N$^1$-methylcyclohexane-1,2-diamine (16b)

The title compounds of Example 16 were prepared according to general procedure A using N-(3-aminopropyl)-morpholine and ketamine.

a.) LC (RT=0.49)/MS: calcd. for $C_{20}H_{32}ClN_3O$: 365.9; obsd.: 365.22 (m+1).
b.) LC (RT=0.86)/MS: calcd. for $C_{20}H_{32}ClN_3O$: 365.9; obsd.: 365.22 (m+1).

Example 17

Trans-1-(2-chlorophenyl)-N$^2$-(3-(4-methylpiperazin-1-yl)propyl)-N$^1$-methylcyclohexane-1,2-diamine (17a), and Cis-1-(2-chlorophenyl)-N$^2$-(3-(4-methylpiperazin-1-yl)propyl)-N$^1$-methylcyclohexane-1,2-diamine (17b)

The title compounds of Example 17 were prepared according to general procedure A using N$^1$-methyl-N$^2$-(3-aminopropyl)-piperazine and ketamine.

a.) LC (RT=0.48)/MS: calcd. for $C_{21}H_{35}ClN_4$: 378.9; obsd.: 378.26 (m+1).
b.) LC (RT=0.69)/MS: calcd. for $C_{21}H_{35}ClN_4$: 378.9; obsd.: 378.26 (m+1).

Example 18

Trans-1-(2-chlorophenyl)-N$^2$-cyclohexyl-N$^1$-methylcyclohexane-1,2-diamine (18a), and Cis-1-(2-chlorophenyl)-N$^2$-cyclohexyl-N$^1$-methylcyclohexane-1,2-diamine (18b)

The title compounds of Example 18 were prepared according to general procedure A using cyclohexylamine and ketamine.

a.) LC (RT=1.55)/MS: calcd. for $C_{19}H_{29}ClN_2$: 320.9; obsd.: 320.19 (m+1).
b.) LC (RT=1.05)/MS: calcd. for $C_{19}H_{29}ClN_2$: 320.9; obsd.: 320.19 (m+1).

Example 19

General Procedure B

Cis-(1R,2R)-1-(2-chlorophenyl)-N$^2$-(3-phenylpropyl)-N$^1$-methylcyclohexane-1,2-diamine (19a), and Cis-(1S,2S)-1-(2-chlorophenyl)-N$^2$-(3-phenylpropyl)-N$^1$-methylcyclohexane-1,2-diamine (19b)

The title compound of Example 15b (110 mg) was purified using high pressure liquid chromatography (HPLC) under the following conditions:
Instrument: JASCO-SFC (SuperCritical Fluid Chromatography) Semi-Prep HPLC (JASCO Inc., Easton, Md., USA).
Stationary Phase: Diacel Chiralpak AS-H, 10 mm column.
Mobile Phase: Ethanol/CO$_2$. Isocratic 5% EtOH/95% CO$_2$.

Detection: UV detection at 220, 254 nM.
Column Temp.: 25° C.
Flow Rate: 2.5 mL/min Fraction 1 (19a): 35 mg. RT=7.187 min, ee>99%, purity >98%.

Fraction 2 (19b): 30 mg. RT=8.347 min, ee>99%, purity >95%. Mass Spectrum: (ESI$^+$ scan) 357.2 $(M_{35Cl}+H)^+$, 359 $(M_{37Cl}+H)^+$.

Example 20

Cis-(1R,2R)-1-(2-chlorophenyl)-N$^2$-(3-(morpholin-1-yl)propyl)-N$^1$-methylcyclohexane-1,2-diamine (20a), and Cis-(1S,2S)-1-(2-chlorophenyl)-N$^2$-(3-(morpholin-1-yl)propyl)-N$^1$-methylcyclohexane-1,2-diamine (20b)

The title compound of Example 16b (60 mg) was purified using high pressure liquid chromatography (HPLC) under the conditions described in Example 19 above.

Fraction 1 (20a): 17 mg. RT=10.192 min, ee>99%, purity >99%.
Mass Spec (ESI+, Acquisition Time=2.546 min): m/z=366.23 (100%, (M+H)$^+$), 368 (33%, (M+H)$^+$ for Cl$^{37}$)

Fraction 2 (20b): 18 mg. RT=12.783 min, ee>99%, purity >99%. Mass Spec (ESI+, Acquisition Time=2.548 min): m/z=366.23 (100%, (M+H)$^+$), 368 (33%, (M+H)$^+$ for Cl$^{37}$).

Determination of Biological Activity

T. brucei brucei Assay

The growth inhibition assay for *T. brucei brucei* was conducted as described previously by Z. B. Mackey (Kenny K. H. Ang, Joseline Ratnam, Jiri Gut, Jennifer Legac, Elizabeth Hansell, Zachary B. Mackey, Katarzyna M. Skrzypczynska, Anjan Debnath, Juan C. Engel, Philip J. Rosenthal, James H. McKerrow, Michelle R. Arkin, Adam R. Renslo (2010) "Mining a Cathepsin Inhibitor Library for New Antiparasitic Drug Leads", *PLoS Neglected Tropical Diseases*, 5(5):e1023). Bloodstream forms of the monomorphic *T. brucei brucei* clone 427-221a were grown in complete HMI-9 medium containing 10% FBS, 10% Serum Plus medium (Sigma Inc., St. Louis, Mo., USA), 50 U/mL penicillin and 50 mg/mL streptomycin (Invitrogen) at 370 C under a humidified atmosphere and 5% CO$_2$. Inhibitor stocks were prepared in 100% DMSO and screened at 5 mM for percent inhibition values or serially diluted from 25 mM to 0.04 mM in 10% DMSO for IC50 determinations. Five mL of each dilution was added to 95 mL of diluted parasites (16104 cells per well) in sterile Greiner 96-well flat white opaque culture plates such that the final DMSO concentration was 0.5%. The 0% inhibition control wells contained 0.5% DMSO while 100% inhibition control wells contained 50 mM thimerosal (Sigma-Aldrich, St. Louis, Mo.). After compound addition, plates were incubated for 40 hours at 370 C. At the end of the incubation period, 50 mL of CellTiter-Glo™ reagent (Promega Inc., Madison, Wis., USA) was added to each well and plates were placed on an orbital shaker at room temperature for 2 min to induce lysis. After an additional 10 min of incubation without shaking, to stabilize the signal, the ATP-bioluminescence of each well was determined using an Analyst HT Plate Reader (Molecular Devices, Sunnyvale, Calif., USA). Raw values were converted to log 10 and percentage inhibition calculated relative to the controls. IC50 curve fittings were performed with Prism 4 software as above. Pentamidine was used as a comparator in the assay.

*Plasmodium falciparum* Activity Assay

*P. falciparum* strain 3D7 was cultured according to the method of Trager and Jensen (W. Trager, J. B. Jensen (1976) "Human malaria parasites in continuous culture", Science, 193(4254):673-5) with minor modifications. Parasites were grown in human erythrocytes (2% hematocrit) in an atmosphere of 5% CO$_2$, 5% O$_2$, 90% N$_2$ in RPMI 1640 medium (Gibco) supplemented with 25 mM hepes buffer (Sigma), 25 mg/L gentamicin (Gibco, Life Technologies, Grand Island, N.Y.), 1 mM sodium pyruvate (Sigma), 50 mg/L hypoxanthine (Sigma), 2 g/L glucose (Sigma), 2.52 g/L sodium bicarbonate (Sigma) and 5 g/L Albumax 1 (Gibco). In vitro antimalarial activity was determined by the SYBR Green I method described by Smilkstein (Smilkstein M, Sriwilaijaroen N, Kelly J X, Wilairat P, Riscoe M. (2004) "Simple and inexpensive fluorescence-based technique for high-throughput antimalarial drug screening". *Antimicrob. Agents Chemother.*, 48(5):1803-6. PMCID: 400546) with modifications (see Winter R W, Kelly J X, Smilkstein M J, Dodean R, Bagby G C, Rathbun R K (2006) "Evaluation and lead optimization of anti-malarial acridones". *Exp. Parasitol.*, 114(1):47-56). Stock solutions of each compound were prepared in DMSO at a concentration of 10 mM and 3-fold serial dilutions were prepared in DMSO for an eleven point curve. Drugs were then diluted 250-fold into culture medium in 96-well storage plates to create 2× drug solutions. Drug solutions (50 μl/well) were transferred in quadruplicate to parasite cultures (50 μl) in 96-well black tissue culture plates for a total volume of 100 μl at 2% hematocrit, 0.2% parasitemia and 0.2% DMSO final concentrations. The plates were then incubated for 72 h at 37° C. After incubation, 100 μl of lysis buffer containing 0.2 μl/ml SYBR Green I was added to each well. After incubation for 1 h at room temperature in the dark, plates were read on a Safire2 (Tecan) plate reader with excitation and emission wavelengths of 497 and 520 nM, respectively. The 50% inhibitory concentrations (IC$_{50}$) were determined by nonlinear regression using a four parameter logistic equation (GraphPad Prism software).

| Data | | |
|---|---|---|
| Compound Example | T. b. brucei IC50 (μM)* | P. falciparum IC50 (μM) |
| 12a | 16.0 | n.d. |
| 15b | 4.6 | 2.5 |
| 16b | 1.7 (1.2-2.4) | 18.0 | n.d.—not determined
*95% Confidence Intervals in parentheses

The invention claimed is:
1. A compound of the formula (I):

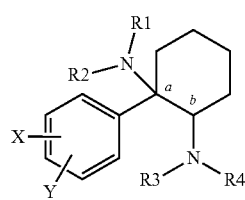

or the pharmaceutically acceptable salt(s) thereof, wherein:
X and Y are independently selected from the group consisting of H, F, Cl, Br, I, CN, OH, CF$_3$, C$_2$F$_5$, C$_1$-C$_6$- alkyl, $C_3$-$C_7$-cycloalkyl, $C_1$-$C_3$-alkoxy, aryl, heteroaryl, —(—C═O)—R5, —NH—(C═O)—R5, —NR5-(C═O)—R6, —(C═O)—NHR5 and —(C═O)—NR5R6.

R1 is hydrogen;
R2 is hydrogen or $C_1$-$C_6$-alkyl;
R3 is hydrogen or $C_1$-$C_6$-alkyl;
R4 is selected from the group consisting of $C_1$-$C_6$-alkyl, $C_3$-$C_7$-cycloalkyl and $(CH_2)_n$—R7, or
NR3R4 is a 5- to 12-membered cyclic or bicyclic ring system containing up to two additional heteroatoms in the ring, selected from N, O and S;
R5 is selected from $C_1$-$C_6$-alkyl and aryl;
R6 is selected from $C_1$-$C_6$-alkyl and aryl, or
NR5R6 is a 5- to 12-membered cyclic or bicyclic ring system containing up to two additional heteroatoms in the ring, selected from N, O and S;
R7 is independently selected from the group consisting of H, $C_1$-$C_6$-alkyl, $C_3$-$C_7$-: cycloalkyl, $(C_1$-$C_6$-alkyloxy)-, $(C_1$-$C_6$-alkyloxy)-$(C_1$-$C_6$-alyl)-, NR8R9-, NR8R9-$(C_1$-$C_6$-alkyl), -aryl, heterocyclyl and heteroaryl; and
R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S; and
n is an integer between 0 and 6.

2. A compound of claim 1, wherein R1 is hydrogen and R2 is methyl.

3. A compound of claim 1, wherein R3 is hydrogen.

4. A compound of claim 1, wherein X is 2-chloro.

5. A compound of claim 1, wherein Y is hydrogen.

6. A compound of claim 1, wherein R4 is $C_1$-$C_6$-alkyl, $C_3$-$C_7$-cycloalkyl or $(CH_2)_n$—R7 (where n is an integer between 0 and 6).

7. A compound of claim 1, wherein R7 is selected from the group consisting of H, $C_1$-$C_6$-alkyl, $C_3$-$C_7$-cycloalkyl, $(C_1$-$C_6$-alkyloxy)-$(C_1$-$C_6$-alkyl)-, NR8R9-$(C_1$-$C_6$-alkyl)-, aryl, heterocyclyl and heteroaryl.

8. A compound of claim 1, wherein each of the individual nitrogen atoms attached at positions "a" and "b" are cis relative to each other.

9. A compound of claim 1, wherein X is 2-chloro, Y is hydrogen, R1 is hydrogen, R2 is methyl and R3 is hydrogen.

10. A compounds of formula I according to claim 1, wherein the compound is selected from:
Trans-1-(2-chlorophenyl)-$N^2$-(2-(dimethylamino)ethyl)-$N^1$-methylcyclo-hexane-1,2-diamine;
Cis-1-(2-chlorophenyl)-$N^2$-(2-(dimethylamino)ethyl)-$N^1$-methylcyclo-hexane-1,2-diamine;
Trans-1-(2-chlorophenyl)-$N^2$-cyclopropyl-$N^1$-methylcyclohexane-1,2-diamine;
Cis-1-(2-chlorophenyl)-$N^2$-cyclopropyl-$N^1$-methylcyclohexane-1,2-diamine;
Trans-1-(2-chlorophenyl)-$N^2$-cyclopentyl-$N^1$-methylcyclohexane-1,2-diamine;
Cis-1-(2-chlorophenyl)-$N^2$-cyclopentyl-$N^1$-methylcyclohexane-1,2-diamine;
Trans-1-(2-chlorophenyl)-$N^2$-(3-methoxypropyl)-$N^1$-methylcyclohexane-1,2-diamine;
Cis-1-(2-chlorophenyl)-$N^2$-(3-methoxypropyl)-$N^1$-methylcyclohexane-1,2-diamine;
Trans-1-(2-chlorophenyl)-$N^1$-methyl-$N^2$-(tetrahydrofuran-2-ylmethyl)cyclohexane-1,2-diamine;
Cis-1-(2-chlorophenyl)-$N^1$-methyl-$N^2$-(tetrahydrofuran-2-ylmethyl)cyclohexane-1,2-diamine;
Cis-1-(2-chloropheny)-$N^2$-(3-(dimethylamino)propyl)-$N^1$-methylcyclohexane-1,2-diamine;
Trans-$N^2$-benzyl-1-(2-chlorophenyl)-$N^1$-methylcyclohexane-1,2-diamine;
Cis-$N^2$-benzyl-1-(2-chlorophenyl)-$N^1$-methylcyclohexane-1,2-diamine;
Cis-1-(2-chlorophenyl)-$N^1$-methyl-$N^2$-(pyridin-4-ylmethyl)cyclohexane-1,2-diamine;
Trans-1-(2-chlorophenyl)-$N^1$-methyl-$N^2$-(pyridin-3-ylmethyl)cyclohexane-1,2-diamine;
Cis-(2-chlorophenyl)-$N^2$-(1-(R)-phenyl)-ethyl)-$N^1$-methylcyclohexane-1,2-diamine;
Trans-(2-chlorophenyl)-$N^2$-(1-(S)-phenyl)-ethyl)-$N^1$-methylcyclohexane-1,2-diamine;
Trans-(2-chlorophenyl)-$N^2$-(3-(1-imidazolyl)-propyl)-$N^1$-methylcyclohexane-1,2-diamine;
Cis-(2-chlorophenyl)-$N^2$-(3-(1-imidazolyl)-propyl)-$N^1$-methylcyclohexane-1,2-diamine;
Trans-(2-chlorophenyl)-$N^2$-(1-ethyl-pyrrolidin-2-ylmethyl)-$N^1$-methylcyclohexane-1,2-diamine;
Cis-(2-chlorophenyl)-$N^2$-(1-ethyl-pyrrolidin-2-ylmethyl)-$N^1$-methylcyclohexane-1,2-diamine;
Trans-(2-chlorophenyl)-$N^2$-(3-(pyrrolidin-1-yl)propyl)-$N^1$-methylcyclohexane-1,2-diamine;
Cis-(2-chlorophenyl)-$N^2$-(3-(pyrrolidin-1-yl)propyl)-$N^1$-methylcyclohexane-1,2-diamine;
Trans-1-(2-chlorophenyl)-$N^2$-(3-phenylpropyl)-$N^1$-methylcyclohexane-1,2-diamine;
Cis-(2-chlorophenyl)-$N^2$-(3-phenyl propyl)-$N^1$-methylcyclohexane-1,2-diamine;
Trans-1-(2-chlorophenyl)-$N^2$-(3-(morpholin-1-yl)propyl)-$N^1$-methylcyclohexane-1,2-diamine;
Cis-1-(2-chlorophenyl)-$N^2$-(3-(morpholin-1-yl)propyl)-$N^1$-methylcyclohexane-1,2-diamine;
Trans-1-(2-chlorophenyl)-$N^2$-(3-(4-methylpiperazin-1-yl)propyl)-$N^1$-methylcyclohexane-1,2-diamine;
Cis-1-(2-chlorophenyl)-$N^2$-(3-(4-methylpiperazin-1-yl) propyl)-$N^1$-methylcyclohexane-1,2-diamine;
Trans-1-(2-chlorophenyl)-$N^2$-cyclohexyl-$N^1$-methylcyclohexane-1,2-diamine; and
Cis-1-(2-chlorophenyl)-$N^2$-(2-(dimethylamino)ethyl)-$N^1$-methylcyclohexane-1,2-diamine.

11. A compounds of formula I according to claim 1, wherein the compound is selected from the group consisting of:
1-(2-chloro-4-methoxyphenyl)-$N^2$-[3-(4,5-dimethyl-1H-imidazol-2-yl)propyl]-$N^1$-methyl-cyclohexane-1,2-diamine;
1-(2-chlorophenyl)-$N^1$-methyl-$N^2$-[3-(1H-1,2,4-triazol-5-yl)propyl]-cyclohexane-1,2-diamine;
1-(2-methylphenyl)-$N^1$-methyl-$N^2$-[3-(3-methyl-1H-1,2,4-triazol-5-yl)propyl]-cyclohexane-1,2-diamine;
1-(2,4-dichlorophenyl)-$N^1$-methyl-$N^2$-[3-(1H-tetrazol-5-yl)propyl]-cyclohexane-1,2-diamine;
1-(3,4-fluorophenyl)-$N^1$-methyl-$N^2$-[2-(1-methyl-1H-tetrazol-5-yl)ethyl]-cyclohexane-1,2-diamine;
1-(4-chlorophenyl)-$N^2$-(2-(dimethylamino)ethyl)-$N^1$-methylcyclohexane-1,2-diamine;
1-(2,4-dichlorophenyl)-$N^2$-(2-(dimethylamino)ethyl)-$N^1$-methylcyclohexane-1,2-diamine;
1-(3,4-difluorophenyl)-$N^2$-(2-(dimethylamino)ethyl)-$N^1$-methylcyclohexane-1,2-diamine;
1-(4-isopropylphenyl)-$N^2$-(2-(dimethylamino)ethyl)-$N^1$-methylcyclohexane-1,2-diamine;
1-(2-methoxyphenyl)-$N^2$-(2-(dimethylamino)ethyl)-$N^1$-methylcyclohexane-1,2-diamine;

1-(2-chlorophenyl)-$N^2$-(2-(dimethylamino)ethyl)-$N^1$-methylcyclohexane-1,2-diamine;

1-(2-chlorophenyl)-$N^2$-[3-(1H-imidazol-2-yl)propyl]-$N^1$-methylcyclohexane-1,2-diamine;

1-(2-chlorophenyl)-$N^2$-[2-(1H-imidazol-2-yl)ethyl]-$N^1$-methylcyclohexane-1,2-diamine;

1-(2-chlorophenyl)-$N^1$-methyl-$N^2$-[3-(1,3-thiazol-2-yl)propyl]-cyclohexane-1,2-diamine;

1-(3,5-dimethyl-2-chlorophenyl)-$N^1$-methyl-$N^2$-[3-(1,3-thiazol-2-yl)propyl]-cyclohexane-1,2-diamine;

1-(3,5-dimethyl-phenyl)-$N^1$-methyl-$N^2$-[3-(4,5-dimethyl-1,3-thiazol-2-yl)propyl]-cyclohexane-1,2-diamine;

1-(2-chlorophenyl)-$N^2$-[3-(1,3-benzothiazol-2-yl)propyl]-$N^1$-methylcyclohexane-1,2-diamine;

1-(2,3-dichlorophenyl)-$N^2$-[3-(1,3-benzimidazol-2-yl)propyl]-$N^1$-methylcyclohexane-1,2-diamine;

1-(3,4-dichlorophenyl)-$N^2$-(2-(3,4-difluorophenyl)ethyl)-$N^1$-methylcyclohexane-1,2-diamine;

1-(2-chlorophenyl)-$N^2$-[(4,5-dimethyl-1H-imidazol-2-yl)methyl]-$N^1$-ethylcyclohexane-1,2-diamine; and 1-(2-chlorophenyl)-$N^1$-ethyl-$N^2$-[(1-methyl-1H-imidazol-2-yl)methyl]cyclohexane-1,2-diamine.

12. A pharmaceutical composition comprising a compound of formula I as described in claim 1, or a pharmaceutically acceptable salt thereof, and a pharmaceutically acceptable carrier.

13. A method of treatment of a disorder or condition selected from the group consisting of Human African Trypanosomiasis, Chagas disease, Malaria and Leishmaniasis, the method comprising administering to a mammal in need of such treatment an amount of a compound of formula I, or a pharmaceutically acceptable salt thereof, as described in claim 1, that is effective in treating such disorder of condition.

14. The method of claim 13 wherein the mammal is a human.

* * * * *